US006572868B1

(12) United States Patent
Cope

(10) Patent No.: US 6,572,868 B1
(45) Date of Patent: Jun. 3, 2003

(54) RESTRUCTURING COMPLEX FOR COSMETIC COMPOSITIONS

(76) Inventor: Sandra E. Cope, 626 N. Washington St., Alexandria, VA (US) 22314

( * ) Notice: Subject to any disclaimer, the term of this patent is extended or adjusted under 35 U.S.C. 154(b) by 0 days.

(21) Appl. No.: 09/620,543

(22) Filed: Jul. 25, 2000

(51) Int. Cl.[7] .............................. A61K 7/08; A61K 6/00; A61K 39/385; A23L 1/05
(52) U.S. Cl. .................... 424/400; 424/70.24; 424/401; 424/195.1; 426/573; 252/89.1
(58) Field of Search .............. 424/70.24, 401, 424/195.1; 252/89.1; 426/573

(56) References Cited

U.S. PATENT DOCUMENTS

| | | | | |
|---|---|---|---|---|
| 4,826,700 A | * | 5/1989 | Bayerlein et al. | 426/573 |
| 5,653,970 A | * | 8/1997 | Vermeer | 424/70.24 |
| 5,939,082 A | * | 8/1999 | Oblong et al. | 424/401 |
| 6,146,637 A | * | 11/2000 | Amari | 424/195.1 |

* cited by examiner

Primary Examiner—Jose' G. Dees
Assistant Examiner—Robert DeWitty
(74) Attorney, Agent, or Firm—Elizabeth J. Pawlak

(57) ABSTRACT

A natural, organic, curative, skin restructuring cosmetic complex for a composition according to the present invention provides very effective retexturization of the skin, producing significantly improved smoothness, as well as significantly increasing the firmness and moisture content of the skin and regulating wrinkles in and/or degeneration of human skin, together with improving overall tone of the skin and decreasing the level of free radicals in the skin. The restructuring composition comprises safe and effective amounts of carrageenans, borage seed oil, squalane, ceramide 3, ceramide 6, red algae extract, dipalmitoyl hydroxyproline and oleuropein, while maintaining their optimum stability.

14 Claims, No Drawings

RESTRUCTURING COMPLEX FOR COSMETIC COMPOSITIONS

BACKGROUND OF THE INVENTION

1. Field of the Invention

The invention relates to a novel and remarkable restructuring complex for cosmetic compositions, particularly those in a lotion, gel and cream form.

2. The Related Art

While the causes underlying the skin aging are not yet completely understood, the market place is flooded with anti-aging formulations. Perhaps this plethora intimates that not all compositions are equally effective in preventing or delaying of skin aging. Indeed, most of these formulations are effective in either decreasing the level of free radicals in the skin or stimulating collagen and glycosaminoglycan synthesis by fibroblasts in the skin, or increasing stratum corneum firmness and flexibility. Although cosmetic industry manufacturers continuously strive to improve the efficacy of anti-aging products by combining several anti-aging ingredients, it is often difficult to combine safe and effective amounts of various active ingredients, while maintaining their optimum stability and effectiveness. Moreover, the products in the prior art typically suffer from the fact that the ingredients most effective for skin moisturization or wrinkle reduction generally are animal-based. Accordingly, it is an object of the present invention to provide a skin restructuring composition which avoids the disadvantages of the prior art insofar as it is comprises only plant-derived ingredients and where effective cell renewal is achieved with substantially no skin irritation during use.

SUMMARY OF THE INVENTION

A new combination of ingredients results in a very effective skin restructuring cosmetic composition for topical applications that, in its basic formulation, provides simultaneously a totally comprehensive hydration, i.e., addressing both water shortage and lipid shortage, protection, calming, and soothing of the skin, and anti-free radical activity, as well as cellulite firming where necessary. The essence of the present invention resides in certain combinations of known materials which synergize and provide a more than additive effect. The basic formulation of a cosmetic composition according to the present invention comprises an aqueous base in which cosmetic components are emulsified and dispersed.

The present invention describes a very effective skin restructuring cosmetic composition for topical applications and a novel method of producing that composition. Moreover, they provide effects not even possible with the individual materials alone or in only partial combination. Briefly stated, the compositions of the present invention contain eight essential ingredients as well as various optional components as indicated below. Each of these components is also present in a quantity sufficient to increase the smoothness and/or firmness of skin to which the composition is applied; these components provide additional beneficial effects. The preparations of the invention are further distinguished over other preparations known to the art in that they are plant-derived-and-virtually-human-skin-identical natural products.

The subject invention also relates to methods for controlling or preventing aging of the skin and which can significantly reduce fatty deposits associated with cellulite, especially in the facial area, by applying to the skin a composition comprising safe and effective amounts of carrageenans, borage oil, squalane, ceramide 3, ceramide 6, red algae extract, dipalmitoyl hydroxyproline, oleuropein and EASHAVE™.

DEFINITIONS

As used herein, "topical application" means directly laying on or spreading on outer skin.

As used herein, "regulating wrinkles" means preventing, retarding, arresting, or reversing the process of wrinkle formation in human skin.

As used herein, "skin atrophy" means the thinning and/or general degradation of the dermis often characterized by a decrease in collagen and/or elastin as well as decreased number, size and increasing potential of fibroblast cells and shrinking of lamellar barrier resulting in the inability to retain moisture. Skin atrophy is a natural result of aging.

As used herein, "regulating skin atrophy" means preventing, retarding, arresting, or reversing the process of atrophy in human skin.

The term "compatible", as used herein, means that the components are capable of being commingled with the essential compounds, and other components of the compositions of the present invention, in a manner such that there is no interaction which would substantially reduce the cosmetic efficacy of the compositions of the present invention under ordinary use situations. Cosmetically-acceptable carrier components must, of course, be of sufficiently high purity and sufficiently low toxicity to render them suitable for administration to the human being treated.

The term "dispersed" refers to any process by which the ingredients are uniformly distributed in the emulsified base, and includes dissolving, emulsifying, and forming a homogenous or colloidal suspension.

Unless otherwise specified, compound names used herein are usually used common names as well as those utilized in the CTFA International Cosmetic Ingredient Dictionary, The Cosmetic, Toiletry, and Fragrance Association, Washington, D.C. (1993), and The U.S. Pharmacopeia, The National Formulary, USP XXII; NF XVII. United States Pharmacopeial Convention, Inc., Rockville, Md., 1990.

As used herein, proportions (percentages) of ingredients are by weight and are based upon the total weight of the relevant composition, unless otherwise indicated. Except where otherwise explicitly indicated, all numbers in this description indicating amounts of material or conditions of reaction, physical properties of materials and/or use are to be understood as modified by the word "about." In Example, the term "qs" means that ingredient is added in a sufficient amount so that the sum of the amounts of all of the ingredients is 100% wt.

Although the novel features of the present.invention are set forth in the appended claims, the invention itself, however, will be best understood from the following detailed description of the invention, including the description of preferred embodiments. These and other objects of this invention will become apparent in light of the following disclosure.

DETAILED DESCRIPTION OF THE INVENTION

The compositions of the present invention comprise nine essential ingredients, to wit, carrageenans, borage oil, squalane, ceramide 3, ceramide 6, red algae extract, dipalmitoyl hydroxyproline, oleuropein and EASHAVE™, as well as various optional components as indicated below. Each of these components is present in a quantity sufficient to increase the smoothness and/or firmness of skin to which the composition is applied; these components provide additional beneficial effects.

Carrageenan is the name given to a family of well-known, linear sulfated polysaccharides obtained from red seaweeds (Rhodophycae), including, Eucheuma cottonii, Eucheuma spinosum, Chondrus crispus, Gigartina stellata, Gigartina acicularis and Gigartina pistillata Furcellaria fastigata, and Ahnfeltia concinna. See The Merck Index, Tenth Edition, on page 260. It is well known that the different types of carrageenan are predominantly developed by different seaweeds at different points in their respective life cycles. The compositions of the present invention generally contain mixtures of individual carrageenans. The carrageenans which can be used in this invention are, for example, lambda, kappa and iota, and intermediate mu carrageenans, and mixtures thereof, preferably containing substantial proportions of the lambda and iota fractions. The ratio between the lambda and iota fractions may vary, while the advantageous results are obtained with a higher proportion of the iota fraction. The purified carrageenans are available readily from numerous commercial sources in the salt form, for example, sodium, calcium, potassium, and the like and are typically colorless, tasteless, odorless, and will create a non-opaque gel in water. The commercial availability of individual carrageenans in a pure form enables the use of specific optimized ratios of the individual types so as to achieve the ultimate moisturizing effect of the final total system to be applied on the skin. The amount of carrageenans in the inventive compositions ranges generally from about 0.1% to about 50% by weight of the composition, preferably from about 10% to about 50%, most preferably from about 40% to about 45%. The molecular weight of the carrageenans will normally be in the range of 5,000 to about 500,000, with most being in the range of about 100,000 to 500,000.

Borage seed oil is obtained from the seeds of borage plant (an herbaceous annual plant), also known as Borago officinalis L. (Boraginaceae) and contains: gamma-linoleic acid, linoleic acid, oleic acid, palmitic acid, sterols, tocopherols, etc. Borage seed oil employed according to the present invention should contain at least 20% of gamma-linolenic acid, either in a free acid form or as its salt or as a mixture thereof. The amount of borage seed oil in the inventive compositions ranges generally from about 0.1% to about 50% by weight of the composition, preferably from about 0.5% to about 10%, most preferably from about 1% to about 2%.

Squalane is a nonocclusive moisturizer and is obtained from olive oil and is commercially available. The amount of squalane in the inventive compositions ranges generally from about 0.1% to about 25% by weight of the composition, preferably from about 0.5% to about 7.5%, most preferably from about 1% to about 3%.

Ceramides are specific sphingolipids which exist in intercellular lipid lamellae of horny layers and play an essential role in structuring and maintaining the lipid-barrier function of the skin. Useful ceramides must be able to penetrate the stratum corneum in order to reach the lipid lamellae of the permeability barrier and must show a high capacity for improvement of the water-retaining capacity of the skin. The compositions of the present invention preferably contain mixtures of the ceramides N-octadecanoyl-phytosphingosine (Ceramide III; INCI name Ceramide 3) and N-(2-hydroxy-octadecanoyl)-phytosphingosine (Ceramide VI; INCI name Ceramide 6) of specific optimized ratios of the individual ceramides. Pure human skin-identical ceramides III and VI which are of a non-animal origin are commercially available from Cosmoferm B.V., Delft, the Netherlands. The amount of Ceramide III in the inventive compositions ranges generally from about 0.05% to about 1% by weight of the composition, preferably from about 0.1% to about 0.5%, most preferably from about 0.1% to about 0.2%. The amount of Ceramide VI in the inventive compositions ranges generally from about 0.05% to about 1% by weight of the composition, preferably from about 0.1% to about 0.5%, most preferably from about 0.1% to about 0.2%.

Dipalmitoyl hydroxyproline is believed to be effective in preventing and/or treating the effects of skin ageing and in firming the skin including for increasing collagen synthesis. The amount of dipalmitoyl hydroxyproline in the inventive compositions ranges generally from about 0.005% to about 5% by weight of the composition, preferably from about 0.075% to about 2%, most preferably from about 0.05% to about 1%.

The next essential of the inventive compositions is an anti-irritant ingredient containing proteinase inhibitors and which is commercially available under the trademark EASHAVE™ from Centerchem, Inc. of Stamford, Conn. It is also believed that this product enhances regeneration of protective lipids. The amount of EASHAVE™ in the inventive compositions ranges generally from about 0.005% to about 10% by weight of the composition, preferably from about 0.01% to about 5%, most preferably from about 0.01% to about 0.5%.

A red algae extract may be obtained from marine red algae selected from a group consisting of Turnerella mertensiana, Schizymenia epiphytica, Turnerella pennyi, Chondrococcus hornemanni, Neodilsea americana, Neodilsea integra and Ahnfeltia concinna. Preferably, it is the butylene glycol (and) Algae Extract (APT) product which is commercially available under the trademark APT from Centerchem, Inc. of Stamford, Conn. and is either bio-engineered or produced by biofermentation from the cells of a strain of red marine algae (Ahnfeltia concinna). This product is believed to increase cell proliferation and to rebuild cells more evenly and to opacify shallow areas. It is also believed that the APT functions with the polysaccharides in the composition to enhance moisturization, soothing and aesthetic characteristics. The amount of red algae extract in the inventive compositions ranges generally from about 0.25% to about 7.5% by weight of the composition, preferably from about 0.5% to about 5%, and even more preferably from about 1.9% to about 2.25%.

Oleuropein is a bitter glucoside found in olives and the roots, leaves and bark of the olive tree, Olea europaea and has been found to protect low density lipoproteins from oxidation (Life Sci 55(24): 1965–71, 1994). A method for extracting oleuropein from olive leaves is disclosed, inter alia, in U.S. Pat. No. 5,714,150 to Nachman, issued Feb. 3, 1998, which is incorporated herein by reference. The amount of oleuropein in the inventive compositions ranges generally from about 0.005% to about 6.5% by weight of the composition, preferably from about 0.005% to about 2.5%, most preferably from about 0.01% to about 0.5%.

The base composition further comprises avocado oil. The amount of avocado oil in the inventive compositions ranges generally from about 0.1% to about 50% by weight of the composition, preferably from about 0.25% to about 20%, more preferably from about 0.5% to about 10%, and most preferably from about 3% to about 6%.

The pH value of the preferred embodiment is from about 4 to about 4.5. If deemed necessary to change or adjust the pH to another value, appropriate cosmetically acceptable primary (acidic or basic) or dual buffer systems may be employed. Exemplary acids include organic acids for example acetic acid, citric acid and tartaric acid, among others, and inorganic phosphoric acid including its salts such as the salts of mono- and di-hydrogen phosphoric acid. The inorganic phosphoric acid salts may also be included in the formulations as buffering agents. Exemplary bases include organic amines, for example, monoethanolamine, triethanolamine, trimethylamine and triethylamine. Thus, a buffering agent may be included within the formulation to maintain the pH at a relatively constant level over time. The determination of which buffering agents to use to obtain the intended formulations, and the determination of the amounts which may be used to achieve the intended buffering effects are well within the capabilities of those skilled in the art without the need for undue experimentation.

If desired, the basic composition can be supplemented with an effective quantity of one or more active plant-derived agents to improve skin condition or reduce fluid retention and/or improve microcirculation, thereby providing a multi-functional restructuring complex, wherein each of said agents is included in a quantity sufficient to retain the composition when it is applied to the skin of an individual in need of such treatment. Examples of such supplements include: (a) the aloe vera gel; (b) aqueous or organic plant extracts, in particular ivy extract, horse chestnut extract, ginseng extract, butcher's broom extract, ginkgo biloba oily extract, horsetail glycolic extract, catchweed glycolic extract, lady's mantle glycolic extract, hawthorn extract, acacia extract, alfalfa extract, bayberry extract, calendula extract, birch extract, bitter orange extract, green tea extract, vine extract, and rosemary extract; (c) oils: jojoba oil, macadamia oil, quinoa oil, soybean oil, sunflower oil, carrot seed oil, cottonseed oil, corn oil, walnut oil, peanut oil, olive oil, almond oil, apricot kernel oil, palm kernel oil, peach kernel oil, sesame oil, coconut oil, cotton seed oil, jojoba oil, bergamot oil; citrus oil; celery seed oil; nutmeg oil, origanum oil, anise oil, cardamom oil, caraway oil, cinnamon oil, clove oil, apricot kernel oil, lavender oil, orange flower oil, tea-tree oil, cocoa butter(theobroma oil), mango butter, shea (karite) butter; (d) plant waxes, such as carnauba or candelilla; (e) enzymes: lactoferrin, lactoperoxidase, glucose oxidase; thiocyanate, superoxide dismutase, glutathione peroxidase and superphycodismutase; (f) coenzymes: coenzyme Q, especially coenzyme Q10; (g) flavonoids; (h) carotenoids; (i) tocopherols; (j) phytoshingosines and sphingolipids; and (k) hydroxy acids; and (l) complexes of vitamins and trace elements. The composition of the present invention can further comprise fragrance and certain chelating agents. The chelating agent may function to chelate any dissolved metals which may be responsible for the in situ generation of oxygen and to enhance the effect of antioxidants. The use of fragrance is well known in the cosmetic art. Preferably, the chelating agent comprises between about 0.001 to about 0.5% of the formulation and most preferably comprises no more than about 0.1% of the formulation and the fragrance comprises about 0.25% of the composition. The determination of which ingredients to use to obtain the intended formulations, and the determination of the amounts which may be used to achieve the intended functions and effects of these ingredients are well within the capabilities of those skilled in the art without the need for undue experimentation. Further information may be obtained on any of these ingredients, for example, by reference to: Balsam, M. S., et al., editors, Cosmetics Science and Technology, 2nd edition, Wiley-Interscience, New York, 1972; Nikitakis, J. M., editor, CTFA Cosmetic Ingredient Handbook, First Edition, published by The Cosmetic, Toiletry and Fragrance Association, Inc., Washington, D.C., 1988; Mukhtar, H, editor, Pharmacology of the Skin, CRC Press 1992; and Green; F. J., The Sigma-Aldrich Handbook of Stains, Dyes and Indicators., Aldrich Chemical Company, Milwaukee Wis. 1991.

Compositions according to the invention can be formulated as a cosmetic composition intended for daily topical application and may be in any form. These forms may include lotions, gels, creams, roll-on formulations, mousses, aerosol sprays and pad-applied formulations.

Preferably the composition is applied to the skin is via topical application of a safe and effective amount of the composition to regulate wrinkles and/or atrophy in human skin and can provide a visible improvement of cellulite-afflicted tissue cellulite after only a few weeks of daily topical application. The amount of actives and frequency of topical application to the skin can vary widely, depending upon personal needs, but it is suggested as an example that topical application range from about once per week to about several times daily, preferably from about twice per week to about 4 times daily, more preferably from about 3 times a week to about 3 times daily, most preferably about once or twice per day.

The following example is provided to further illustrate the present invention and should not be construed to limit the scope of the invention of the present application in any way. Accordingly, the following table provides a preferred range of weight to weight percentages for each essential ingredient present in a highly preferred embodiment for commercial use:

EXAMPLE 1

| INGREDIENT | preferred wt % |
| --- | --- |
| Carrageenans | 40–45 |
| Borage Oil | 1–2 |
| Squalane | 1–3 |
| Ceramide III | 0.1–0.2 |
| Ceramide VI | 0.1–0.2 |
| Red Algae Extract | 1.9–2.25 |
| Dipalmitoyl Hydroxyproline | 0.05–1.00 |
| Oleuropein | 0.01–0.50 |
| EASHAVE | 0.01–0.50 |
| Demineralized Water | qs. |

The manner in which the composition of the present invention is formed is known to those skilled in the art. The ingredients can be combined in a number of sequences and orders. The object of each of the mixing sequences is to prepare a smooth and homogenous composition. The ingredients are loaded in sequences into a steam-lined kettle equipped with a high-speed mixture such as a Lightnin'™ mixer and the sweep mixing speed is set at a rate fast enough not to create air. Some ingredients are pre-mixed to form a slurry and then added to the batch kettle. The determination of the target temperatures for the particular sequences is well within the capabilities of those skilled in the art without the need for undue experimentation. Mixing is continued until the lumps are gone and a smooth cream results and is followed by slow homogenization mixing on the AGI kettle for the remainder of the manufacturing process. The batch is then gradually cooled to 20–25° C. The determination of time length of cooling is well within the capabilities of those skilled in the art without the need for undue experimentation.

While particular embodiments of the present invention have been described, it will be obvious to those skilled in the art that the present invention may, of course, be carried out in other specific ways than those set forth herein without departing from the spirit and essential characteristics of the present invention. The present embodiments are, therefore, to be considered in all respects as illustrative and not restrictive, and to provide for all changes coming within the meaning and equivalency range the appended claims are intended to embrace. It is also to be understood that in said claims, ingredients or compounds recited in the singular are intended to include compatible mixtures of such ingredients wherever the sense permits. It is still further to be understood that the following claims are intended to cover all of the generic and specific features of the invention herein described and all statements of the scope of the invention which, as a matter of language, might be said to fall therebetween.

Accordingly, it is intended to be bound only by the following claims:

What is claimed is:

1. A restructuring cosmetic composition comprising a combination of safe and effective amounts of borage seed oil, squalane, ceramide 3, ceramide 6, red algae extract, dipalmitoyl hydroxyproline, oleuropein, sodium hyaluronate and a mixture of two or more types of carrageenans, said types carrageenans being selected from the group consisting of lambda, kappa, iota and intermediate mu carrageenans and wherein said mixture of two or more types of carrageenans comprises substantial proportions of lambda and iota carrageenans and wherein said iota carrageenan is in a higher proportion than lambda carrageenan.

2. A restructuring cosmetic composition as claimed in claim 1 further comprising at least one additive selected from the group of consisting of: aloe vera gel, ivy extract, horse chestnut extract, ginseng extract, butcher's broom extract, ginkgo biloba oily extract, horsetail glycolic extract, catchweed glycolic extract, lady's mantle glycolic extract, hawthorn extract, acacia extract, alfalfa extract, bayberry extract, calendula extract, birch extract, bitter orange extract, green tea extract, vine extract, rosemary extract, jojoba oil, macadamia oil, quinoa oil, soybean oil, sunflower oil, carrot seed oil, cottonseed oil, corn oil, walnut oil, peanut oil, olive oil, almond oil, apricot kernel oil, palm kernel oil, peach kernel oil, sesame oil, coconut oil, cotton seed oil, jojoba oil, bergamot oil; citrus oil; celery seed oil; nutmeg oil, origanum oil, anise oil, cardamom oil, caraway oil, cinnamon oil, clove oil, apricot kernel oil, lavender oil, orange flower oil, tea-tree oil, cocoa butter(theobroma oil), mango butter, shea (karite) butter, carnauba wax, candelilla wax, lactoferrin, lactoperoxidase, glucose oxidase; thiocyanate, superoxide dismutase, glutathione peroxidase, superphycodismutase, coenzyme Q, coenzyme Q10, flavonoids, carotenoids, tocopherols, phytoshingosines, sphingolipids, hydroxy acids, vitamins and trace elements.

3. A skin cream product comprising the restructuring cosmetic composition of claim 1.

4. A skin cream product comprising the restructuring cosmetic composition of claim 2.

5. A method for restructuring human skin comprising the steps of dispensing the skin cream product of claim 3 and applying said product to human skin.

6. A restructuring cosmetic composition which comprises:
   (a) a mixture of two or more types of carrageenans about 0.1 to about 50 wt %;
   (b) borage seed oil from about 0.1 to about 25 wt %;
   (c) squalane from about 0.1 to about 25 wt %;
   (d) ceramide 3 from about 0.1 to about 0.5 wt %;
   (e) ceramide 6 from about 0.1 to about 0.5 wt %;
   (f) red algae extract from about 0.5 to about 5 wt %;
   (g) dipalmitoyl hydroxyproline from about 0.01 to about 5 wt %;
   (h) oleuropein from about 0.01 to about 5 wt %; and
   (i) sodium hyaluronate sold under the trademark EASHAVE™ from about 0.01 to about 5 wt %; and
   wherein said types carrageenans are selected from the group consisting of lambda, kappa, iota and intermediate mu carrageenans and wherein said mixture of two or more types of carrageenans comprises substantial proportions of lambda and iota carrageenans and wherein said iota carrageenan is in a higher proportion than lambda carrageenan.

7. A restructuring cosmetic composition as claimed in claim 6 wherein said borage seed oil contains at least 20% of gamma-linolenic acid, either in a free acid form or as its salt, or as a mixture thereof.

8. A restructuring cosmetic composition as claimed in claim 6 wherein said red algae extract is an aqueous mixture of butylene glycol and red algae extract obtained from Ahnfeltia concina.

9. A restructuring cosmetic composition as claimed in claim 6 wherein said red algae extract is a bio-engineered product sold under the trademark APT.

10. A restructuring cosmetic composition as claimed in claim 9 wherein said ceramide 3 is a pure human skin-identical ceramide 3 sold under the name CERAMIDE III and wherein said ceramide 6 is a pure human skin-identical ceramide 6 sold under the name CERAMIDE VI.

11. A restructuring cosmetic composition which comprises:
   (a) a mixture of two or more types of carrageenans from about 40 to about 45 wt %;
   (b) borage oil from about 1 to about 2 wt %;
   (c) squalane from about 1 to about 3 wt %;
   (d) ceramide 3 from about 0.1 to about 0.2 wt %;
   (e) ceramide 6 from about 0.1 to about 0.2 wt %;
   (f) red algae extract from about 1.9 to about 2.25 wt %;
   (g) dipalmitoyl hydroxyproline from about 0.05 to about 1.00 wt %;
   (h) oleuropein from about 0.01 to about 0.50 wt %;
   (i) sodium hyaluronate sold under the trademark EASHAVE™ from about 0.01 to about 0.50 wt %; and
   (j) avocado oil from about 0.1 to about 0.50 wt %; and
   wherein said types carrageenans are selected from the group consisting of lambda, kappa, iota and intermediate mu carrageenans and wherein said mixture of two or more types of carrageenans comprises substantial proportions of lambda and iota carrageenans and wherein said iota carrageenan is in a higher proportion than lambda carrageenan.

12. A restructuring cosmetic composition as claimed in claim 6 wherein said red algae extract is a bio-engineered product sold under the trademark APT and wherein said ceramide 3 and ceramide 6 are pure human skin-identical ceramides sold under the name CERAMIDE III an CERAMIDE VI, respectively.

13. A skin cream product comprising the restructuring cosmetic composition of claim 12.

14. A method for restructuring human skin comprising the steps of dispensing the skin cream product of claim 13 and applying said product to human skin.

* * * * *